(12) United States Patent
Chang et al.

(10) Patent No.: US 9,194,872 B2
(45) Date of Patent: Nov. 24, 2015

(54) POTENTIATION OF NANOPHARYNGEAL CANCER RADIOTHERAPY BY INHIBITORS OF LEUKEMIA INHIBITORY FACTOR

(71) Applicant: Chang Gung University, Tao-Yuan (TW)

(72) Inventors: Yu-Sun Chang, Tao-Yuan (TW); Shu-Chen Liu, Tao-Yuan (TW); Ngan-Ming Tsang, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 14/250,834

(22) Filed: Apr. 11, 2014

(65) Prior Publication Data
US 2015/0133376 A1　May 14, 2015

(30) Foreign Application Priority Data

Nov. 8, 2013　(TW) .............. 102140672 A

(51) Int. Cl.
*A61K 38/01*　(2006.01)
*G01N 33/574*　(2006.01)
*A61K 38/17*　(2006.01)

(52) U.S. Cl.
CPC ...... *G01N 33/57488* (2013.01); *A61K 38/1793* (2013.01); *G01N 33/57407* (2013.01); *G01N 2333/5415* (2013.01); *G01N 2800/52* (2013.01)

(58) Field of Classification Search
None
See application file for complete search history.

(56) References Cited

U.S. PATENT DOCUMENTS 8,507,495 B2　8/2013　Liao

FOREIGN PATENT DOCUMENTS

WO　2011109387 A1　9/2011

OTHER PUBLICATIONS

Liu et al., Leukemia inhibitory factor promotes nasopharyngeal carcinoma progression and radioresistance, J. Clin. Investig. 123, 5269-5283, 2013. ePub Nov. 25, 2013.*
McKeown et al., The relationship between circulating concentrations of C-reactive protein, inflammatory cytokines and cytokine receptors in patients with non-small-cell lung cancer. Brit. J. Cancer, 91, 1993-1995, 2004.*
Chen et al., LIFR is a breast cancer metastasis suppressor upstream of the Hippo-YAP pathway and a prognostic marker. Nature Medicine, 18, 1511-1519, 2012.*

* cited by examiner

*Primary Examiner* — Elly-Gerald Stoica
(74) *Attorney, Agent, or Firm* — Osha Liang LLP

(57) ABSTRACT

A method for evaluation of cancer diagnosis following cancer radiotherapy, comprising: providing a serum sample of a cancer patient prior to the cancer radiotherapy; and measuring a leukemia inhibitory factor concentration in the serum sample. Also provided is a method for potentiation of cancer radiotherapy, comprising: administrating a leukemia inhibitory factor inhibitor or a leukemia inhibitory factor receptor inhibitor to a subject in need of the cancer radiotherapy.

4 Claims, 20 Drawing Sheets

POTENTIATION OF NANOPHARYNGEAL CANCER RADIOTHERAPY BY INHIBITORS OF LEUKEMIA INHIBITORY FACTOR

CROSS REFERENCE

This non-provisional application claims priority from Taiwan Patent Application NO. 102140672, filed on Nov. 8, 2013, the content thereof is incorporated by reference herein.

FIELD OF THE INVENTION

The present invention relates to evaluation of cancer diagnosis following cancer radiotherapy, and also relates to potentiation of cancer radiotherapy.

BACKGROUND OF THE INVENTION

As per the statistics up to 2013 provided by the Ministry of Health and Welfare of Taiwan, cancer, also called "malignant tumor," has been the leading cause of death for 31 years. Current clinical treatment for cancer comprises surgical incision, chemotherapy, target therapy, or radiotherapy. Among them, radiotherapy is focused on in the present invention.

Cancer radiotherapy destroys tumor cells of the associated patient by emitting radiation to the tumor cells. Unfortunately, radiation can attack the patient's healthy cells, as well as the tumor cells. To date, a certain pharmaceutical, such as nitroimidazole described in WO2011/109387, and a composition including rapamycin and substituted quinolone described in U.S. Pat. No. 8,507,495, has been found to make tumor cells sensitive to radiation. As such, the dosage of radiation may be reduced and the risk of attacking healthy cells by radiation may be diminished. As a result, the efficiency of attacking tumor cells by radiation may be improved. The pharmaceutical is particularly called "sensitizer for cancer radiotherapy," but it usually has low biocompatibility.

Accordingly, there is a need to develop a novel pharmaceutical to be employed as a sensitizer for cancer radiotherapy, and to be expected to bring more selections for the radiotherapy.

SUMMARY OF THE INVENTION

A first aspect of the present invention is to provide a method for evaluation of cancer diagnosis following cancer radiotherapy. The provided method comprises the following steps of: providing a serum sample of a cancer patient prior to the cancer radiotherapy; and measuring a concentration of leukemia inhibitory factor in the serum sample.

A second aspect of the present invention is to provide a method for potentiation of cancer radiotherapy. The provided method comprises the following step of: administrating a leukemia inhibitory factor inhibitor to a subject in need of the cancer radiotherapy.

A third aspect of the present invention is to provide a method for potentiation of cancer radiotherapy. The provided method comprises the step of: administrating a leukemia inhibitory factor receptor inhibitor to a subject in need of the cancer radiotherapy.

DETAILED DESCRIPTION OF THE INVENTION

Figure 1A:
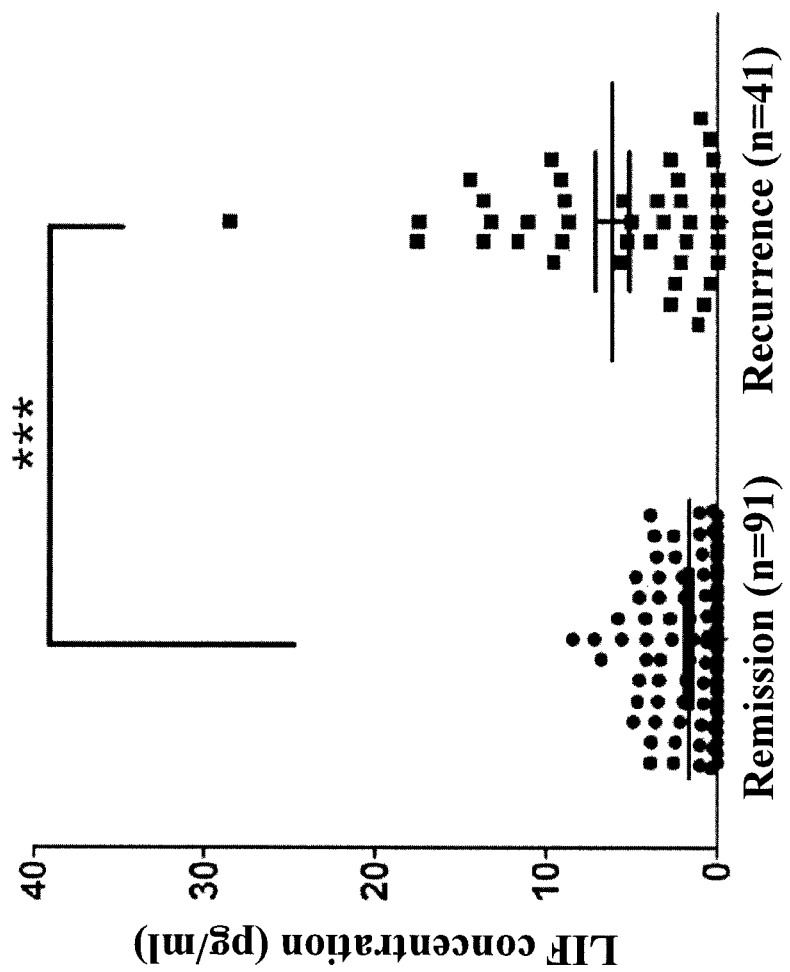
FIG. 1A is a statistical graph showing the relationship of a leukemia inhibitory factor concentration in a serum sample of a nasopharyngeal cancer patient prior to cancer radiotherapy, and cancer diagnosis following the radiotherapy.

In order to understand the description of the content, the used terminology therein is defined as follows:

The term "leukemia inhibitory factor (LIF)" is a cytokine belonging to the interleukin-6 family and mediating cell growth through inhibition of cell differentiation.

The term "leukemia inhibitory factor receptor (LIFR)," also called cluster differentiation 118 (CD118), is a transmembrane protein which can bind leukemia inhibitory factor to activate a series of signal transduction in a cell.

The term "inhibitor" is a substance to inhibit the activity of a certain factor. Therefore, a leukemia inhibitory factor inhibitor can inhibit the leukemia inhibitory factor activity; a leukemia inhibitory factor receptor inhibitor can inhibit the leukemia inhibitory factor receptor activity.

The term "soluble receptor" is a non-transmembrane protein to bind a certain factor. Therefore, a soluble leukemia inhibitory factor receptor (sLIFR) can bind leukemia inhibitory factor.

The term "antibody" is a Y-shaped protein which is made of two heavy chains and two light chains linked to the heavy chain via a disulfide bond, and can recognize and neutralize a certain antigen. Therefore, a leukemia inhibitory factor antibody can recognize and neutralize leukemia inhibitory factor; a leukemia inhibitory factor receptor antibody can recognize and neutralize a leukemia inhibitory factor receptor.

The term "siRNA" is a double-strand RNA having a length of 20-25 nucleotides to specifically interfere with expression of a certain gene. Therefore, a leukemia inhibitory factor siRNA can interfere with leukemia inhibitory factor expression; a leukemia inhibitory factor receptor siRNA can interfere with leukemia inhibitory factor receptor expression.

The term "antagonist" is a substance to compete with a certain factor. Therefore, a leukemia inhibitory factor antagonist can compete with leukemia inhibitory factor.

In the present invention, when a patient suffering from nasopharyngeal cancer has a high leukemia inhibitory factor concentration in a serum sample thereof prior to cancer radiotherapy, the cancer is diagnosed with a recurrence tendency after the cancer radiotherapy. On the other hand, when the patient has a low leukemia inhibitory factor concentration in the serum sample prior to the cancer radiotherapy, the cancer is diagnosed with a remission tendency after the cancer radiotherapy. Additionally, a soluble leukemia inhibitory factor receptor is further found to sensitize a nasopharyngeal cancer cell to radiation so that the cell growth is repressed. At least for these reasons, blocking a leukemia inhibitory factor receptor of the nasopharyngeal cancer cell from binding to leukemia inhibitory factor can keep the cancer cell more sensitive to radiation leading to repression of cancer cell growth.

A first embodiment with accordance to the present invention discloses a method for evaluation of cancer diagnosis following cancer radiotherapy. The method comprises: providing a serum sample of a cancer patient prior to the cancer radiotherapy; and measuring a concentration of leukemia inhibitory factor in the serum sample. As described in the following examples, when the leukemia inhibitory factor concentration is higher than 4.96 pg/ml, the cancer is diagnosed with the probability of recurrence after the radiotherapy; when the leukemia inhibitory factor concentration is lower than 4.96 pg/ml, the cancer is diagnosed with the probability of remission after the radiotherapy. The term "recurrence" in this content means that the symptom of a disease is eliminated during treatment for the disease, but recovered during a tracking period after this treatment. The term "remission" in the content means that the symptom of a disease is eliminated during treatment for the disease and during a tracking period after this treatment.

In this embodiment, the cancer is, for example but not limited to, a solid tumor cancer. An example of the solid tumor cancer is breast cancer, lung cancer, hepatic cancer, buccal cancer, gastric cancer, colon cancer, nasopharyngeal cancer, skin cancer, renal cancer, brain cancer, prostate cancer, ovarian cancer, cervical cancer, intestinal cancer, or bladder cancer, and preferably is nasopharyngeal cancer.

A second embodiment with accordance to the present invention discloses a method for potentiation of cancer radiotherapy. The method comprises: administrating a leukemia inhibitory factor inhibitor to a subject in need of the cancer radiotherapy. In the subject, the leukemia inhibitory factor inhibitor can avoid a leukemia inhibitory factor receptor of his/her tumor from binding to leukemia inhibitory factor by inhibiting leukemia inhibitory factor activity. By such a way, the subject's tumor is so sensitive to radiation used in the radiotherapy that the efficiency of the cancer radiotherapy is improved.

In this embodiment, the leukemia inhibitory factor inhibitor is, for example but not limited to, a soluble leukemia inhibitory factor receptor, a leukemia inhibitory factor antibody, a leukemia inhibitory factor siRNA, or a leukemia inhibitory factor antagonist, and preferably is a soluble leukemia inhibitory factor receptor.

In this embodiment, the cancer is, for example but not limited to, a solid tumor cancer. An example of the solid tumor cancer is breast cancer, lung cancer, hepatic cancer, buccal cancer, gastric cancer, colon cancer, nasopharyngeal cancer, skin cancer, renal cancer, brain cancer, prostate cancer, ovarian cancer, cervical cancer, intestinal cancer, or bladder cancer, and preferably is nasopharyngeal cancer.

It is noted that the leukemia inhibitory factor inhibitor may be in various pharmaceutical forms, such as a tablet, a capsule, a granule, a powder, a fluid extract, a solution, a syrup, a suspension, an emulsion, a tincture, or an intravenous injection. A doctor can determine the dose, time, and route thereof to be administrated according to the subject's general condition and the cancer radiotherapy course. Generally, the leukemia inhibitory factor inhibitor may be administrated to the subject prior to, during, or following the cancer radiotherapy. Furthermore, the leukemia inhibitory factor inhibitor may be administrated to the subject intravascularly, intraspinally, intramuscularly, subcutaneously, intraperitoneally, orally, rectally, vaginally, intranasally, or intratumorally.

A third embodiment with accordance to the present invention discloses a method for potentiation of cancer radiotherapy. The method comprises: administrating a leukemia inhibitory factor receptor inhibitor to a subject in need of the cancer radiotherapy. In the subject, the leukemia inhibitory factor receptor inhibitor can avoid a leukemia inhibitory factor receptor of his/her tumor from binding to leukemia inhibitory factor by inhibiting the activity of the leukemia inhibitory factor receptor. By such a manner, the subject's tumor is so sensitive to radiation used in the cancer radiotherapy that the efficiency of the radiotherapy is improved.

In this embodiment, the leukemia inhibitory factor receptor inhibitor is, for example but not limited to, a leukemia inhibitory factor receptor antibody, or a leukemia inhibitory factor receptor siRNA.

In this embodiment, the cancer is, for example but not limited to, a solid tumor cancer. An example of the solid tumor cancer is breast cancer, lung cancer, hepatic cancer, buccal cancer, gastric cancer, colon cancer, nasopharyngeal cancer, skin cancer, renal cancer, brain cancer, prostate cancer, ovarian cancer, cervical cancer, intestinal cancer, or bladder cancer, and preferably is nasopharyngeal cancer.

It is also noted that the leukemia inhibitory factor receptor inhibitor may be in various pharmaceutical forms, such as a tablet, a capsule, a granule, a powder, a fluid extract, a solution, a syrup, a suspension, an emulsion, a tincture, or an intravenous injection. A doctor can determine its dose, time, and route to be administrated according to the subject's general condition and the course of the cancer radiotherapy. Generally, the leukemia inhibitory factor receptor inhibitor may be administrated to the subject prior to, during, or following the cancer radiotherapy. Furthermore, the leukemia inhibitory factor receptor inhibitor may be administrated to the subject intravascularly, intraspinally, intramuscularly, subcutaneously, intraperitoneally, orally, rectally, vaginally, intranasally, or intratumorally.

The following examples are offered to further illustrate the embodiments of the present invention.

EXAMPLE 1

Relationship of a Leukemia Inhibitory Factor Concentration in a Serum Sample of a Nasopharyngeal Cancer Patient Prior to Cancer Radiotherapy, and Cancer Diagnosis Following the Cancer Radiotherapy Firstly, 132 nasopharyngeal cancer patients' serum samples prior to cancer radiotherapy were obtained. Then, all the patients completely underwent the cancer radiotherapy, the dosage thereof was 6840-7600 cGy/7-8 weeks. During a tracking period after the radiotherapy, the nasopharyngeal cancer of all patients was diagnosed with recurrence or remission. As shown in FIG. 1A, the nasopharyngeal cancer of 91 patients was diagnosed with remission, and the nasopharyngeal cancer of the other 41 patients was diagnosed with recurrence. Additionally, the leukemia inhibitory factor concentration in the serum samples of patients suffering from nasopharyngeal cancer diagnosed with remission was substantially lower than that diagnosed with recurrence.

Figure 1B:
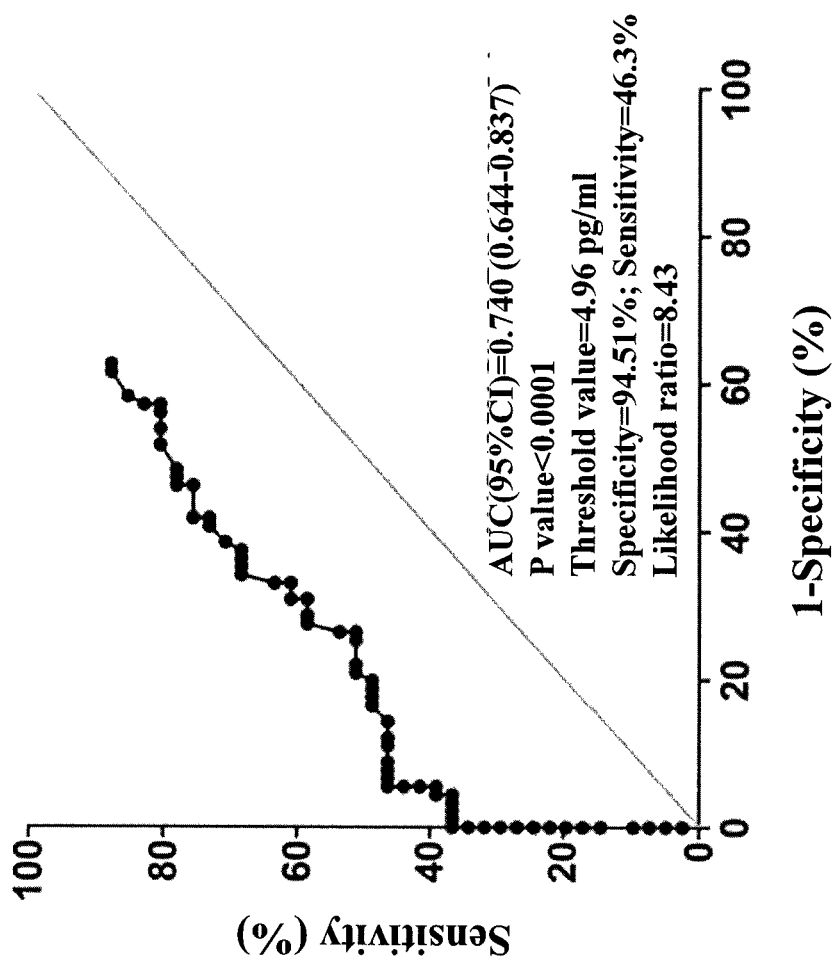
FIG. 1B is a graph of receiver operating characteristic curve presenting the relationship of a leukemia inhibitory factor concentration in a serum sample of a nasopharyngeal cancer patient prior to cancer radiotherapy, and cancer diagnosis following the radiotherapy.

As shown in FIG. 1B, a receiver operating characteristic curve was made based on the leukemia inhibitory factor concentration in the serum samples of the 132 patients, and the diagnosis data. When the leukemia inhibitory factor concentration is 4.96 pg/ml, this value can be employed to evaluate nasopharyngeal cancer to be diagnosed with recurrence or remission after the radiotherapy.

Figure 1C:
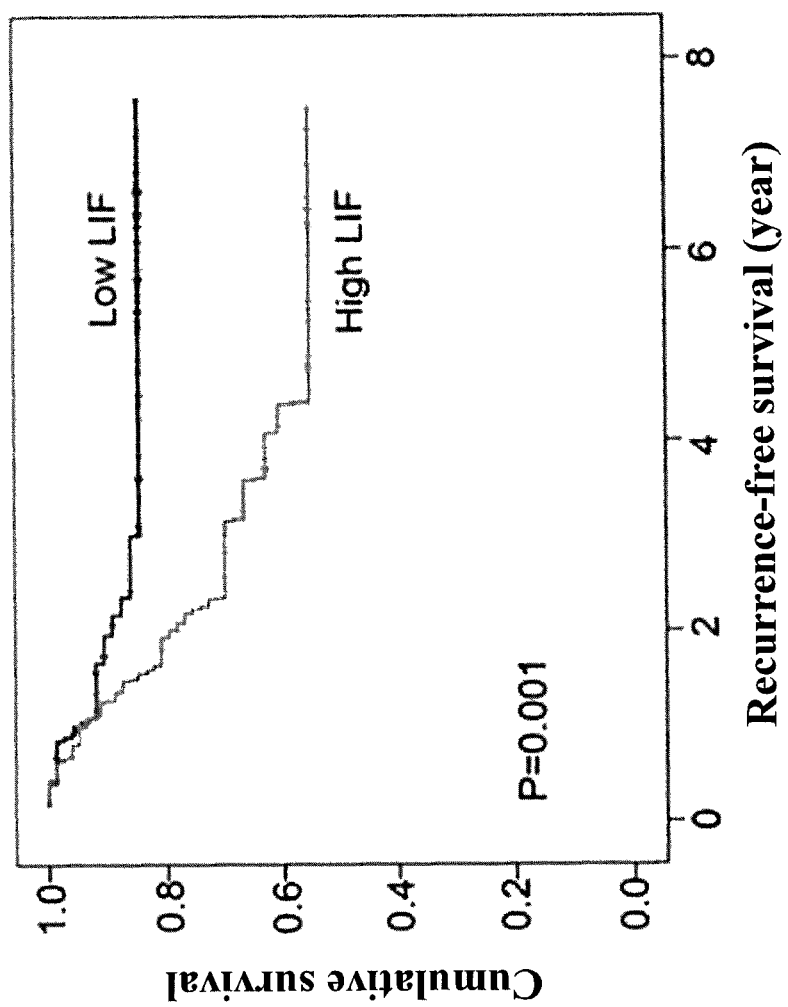
FIG. 1C is a statistical graph illustrating the relationship of a leukemia inhibitory factor concentration in a serum sample of a nasopharyngeal cancer patient prior to cancer radiotherapy, and recurrence-free survival of the patient.
Figure 1D:
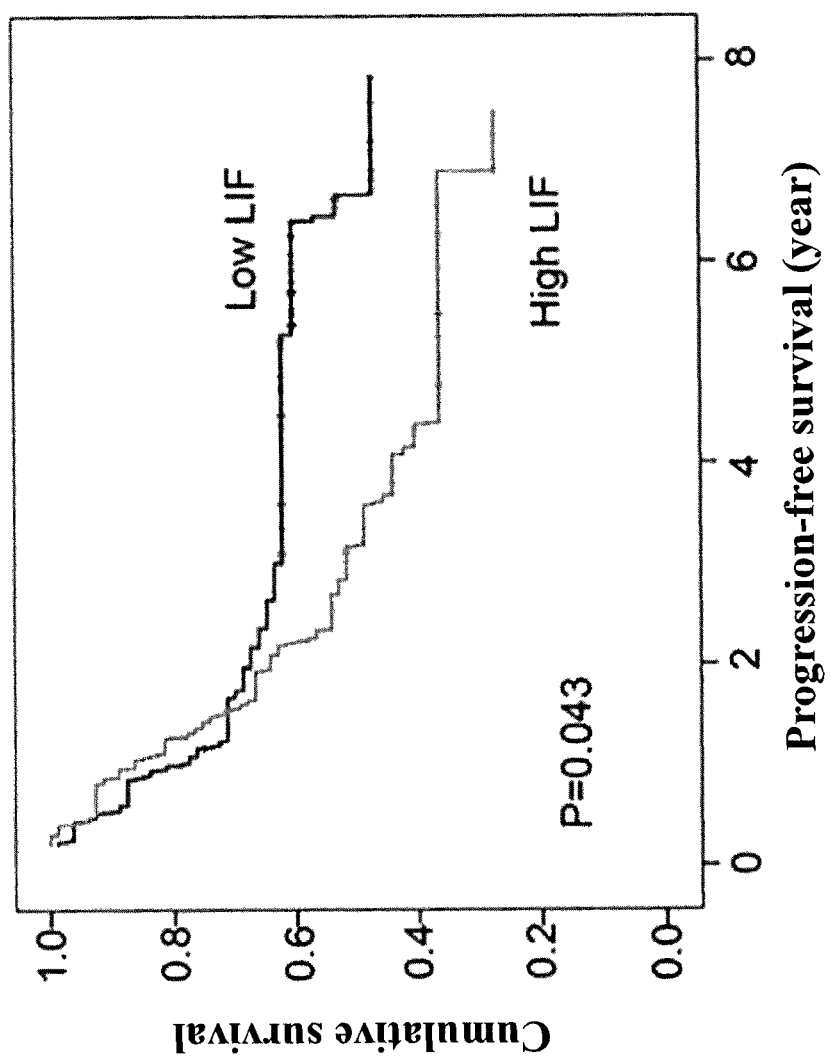
FIG. 1D is a statistical graph clarifying the relationship of a leukemia inhibitory factor concentration in a serum sample of a nasopharyngeal cancer patient prior to cancer radiotherapy, and progression-free survival of the patient.

The 132 patients were further divided into two groups: high LIF group and low LIF group. The leukemia inhibitory factor concentration in the serum samples of high LIF group patients was higher than 4.96 pg/ml, and that of low LIF group patients was lower than 4.96 pg/ml. As shown in FIGS. 1C and 1D, the high LIF group patients have short recurrence-free survival and short progression-free survival relative to the low LIF group patients.

As detailed above, a leukemia inhibitory factor concentration in a serum sample of a nasopharyngeal cancer patient prior to cancer radiotherapy can be a standard to diagnose the cancer with recurrence or remission after the cancer radiotherapy.

EXAMPLE 2

Figure 2A:
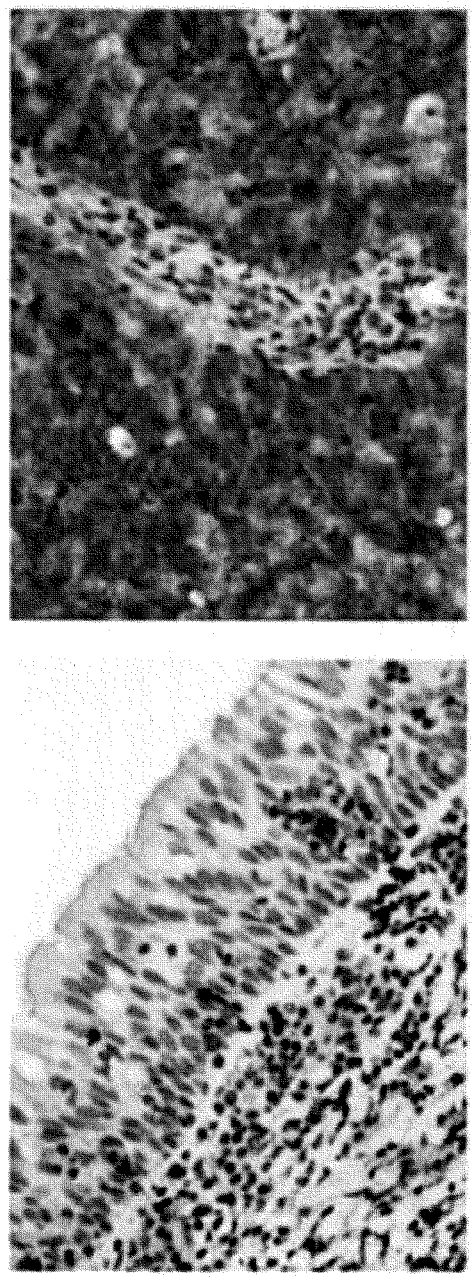
FIG. 2A is a photo of immunohistochemical staining displaying the expression of leukemia inhibitory factor in a nasopharyngeal tumor tissue of a nasopharyngeal cancer patient, and that in a nasopharyngeal normal tissue thereof.
Figure 2B:
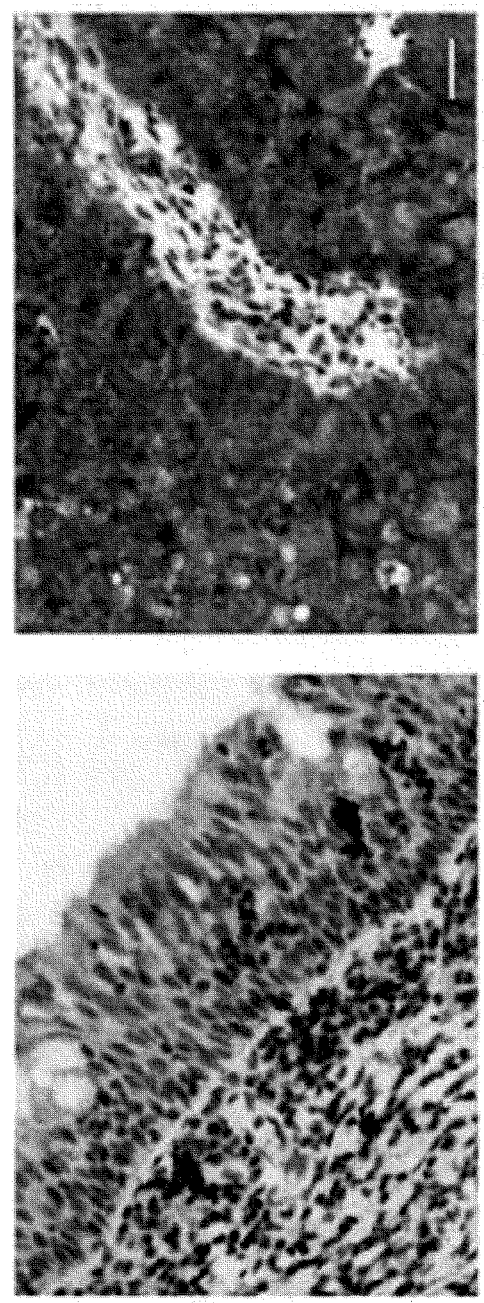
FIG. 2B is a picture of immunohistochemical staining showing the expression of a leukemia inhibitory factor receptor in a nasopharyngeal tumor tissue of a nasopharyngeal cancer patient, and that in a nasopharyngeal normal tissue thereof.

Expression of Leukemia Inhibitory Factor and its Receptor in a Nasopharyngeal Tumor Tissue of a Nasopharyngeal Cancer Patient, and that in the Patient's Nasopharyngeal Normal Tissue Firstly, an immunohistochemical staining was practiced to stain a nasopharyngeal tumor tissue of a nasopharyngeal cancer patient and a nasopharyngeal normal tissue thereof. As shown in FIGS. 2A and 2B, the leukemia inhibitory factor expression level in a nasopharyngeal tumor tissue is higher than that in a nasopharyngeal normal tissue, and the leukemia inhibitory factor receptor expression level in a nasopharyngeal tumor tissue is also higher than that in a nasopharyngeal normal tissue.

Figure 2C:
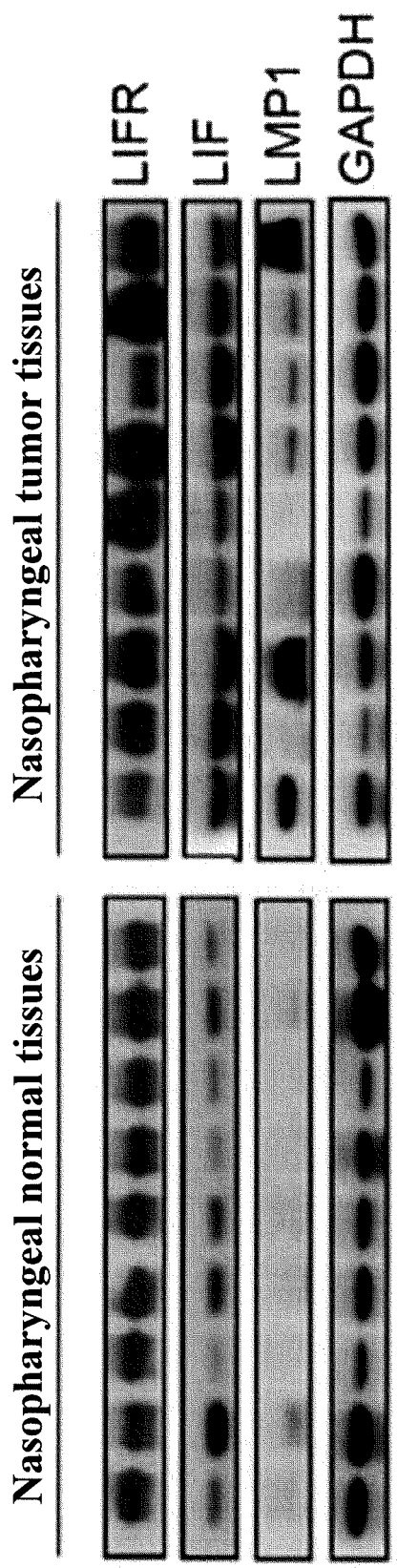
FIG. 2C is a Western blotting result presenting the expression of leukemia inhibitory factor and its receptor in a nasopharyngeal tumor tissue of a nasopharyngeal cancer patient, and that in a nasopharyngeal normal tissue thereof.

A Western blotting was practiced to further confirm the foregoing result. Similarly, the leukemia inhibitory factor expression level in a nasopharyngeal tumor tissue is higher than that in a nasopharyngeal normal tissue, and the leukemia inhibitory factor receptor expression level in a nasopharyngeal tumor tissue is higher than that in a nasopharyngeal normal tissue (FIG. 2C).

According to this example, the microenvironment of a nasopharyngeal tumor tissue of a nasopharyngeal cancer patient contains plenty of leukemia inhibitory factor and their receptors.

EXAMPLE 3

Effect of Leukemia Inhibitory Factor on the Growth of a Nasopharyngeal Cancer Cell In Vivo or In Vitro $6 \times 10^3$ TW06 cells were seeded, and then cultivated at 37° C. overnight. These cells were treated with PBS, a soluble leukemia inhibitory factor receptor (1 μg/ml), leukemia inhibitory factor (10 ng/ml), or a soluble leukemia inhibitory factor receptor plus leukemia inhibitory factor. After which, an xCelligence real time cell analyzer (Roche Applied Science) was used to detect the cell growth at a certain time point after this treatment.

Figure 3A:
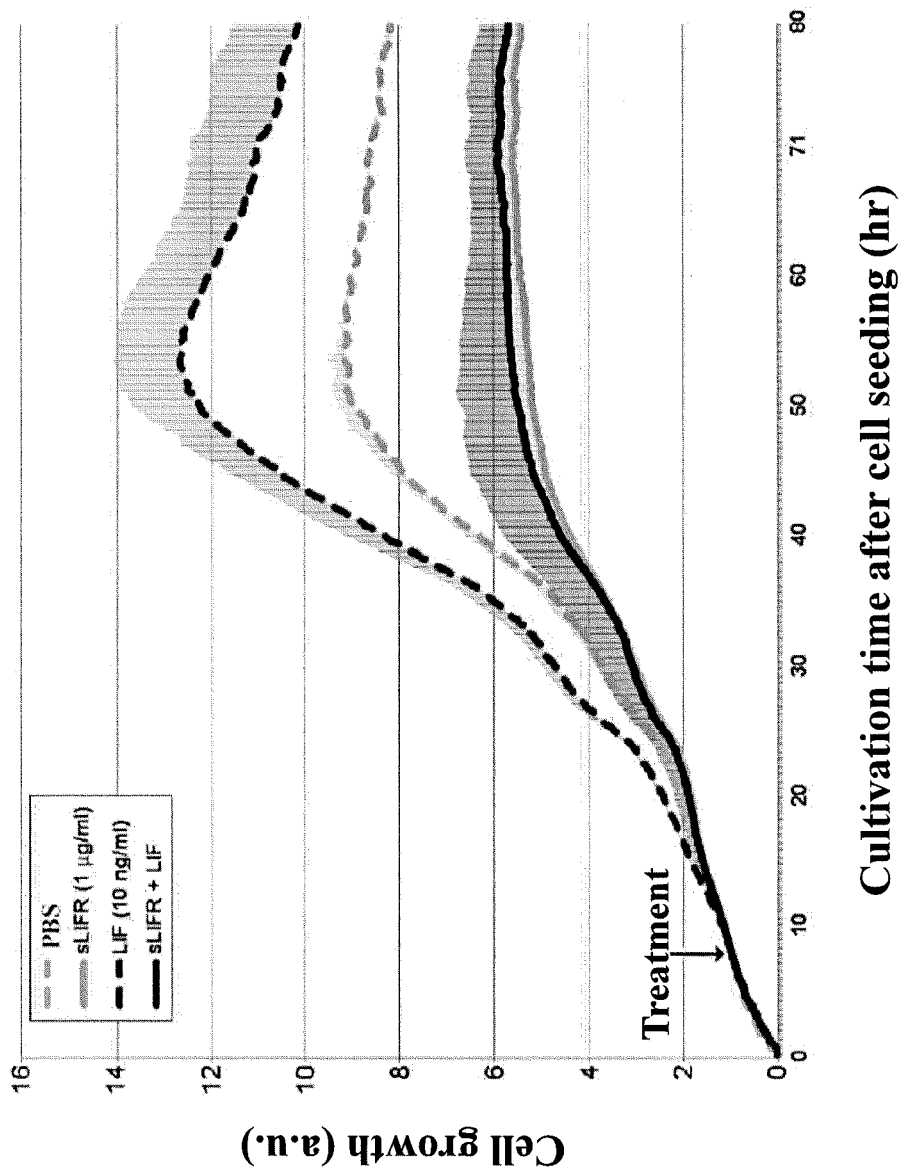
FIG. 3A is a graph illustrating the growth of a nasopharyngeal cancer cell with various substance treatment.

As shown in FIG. 3A, the growth of cells with leukemia inhibitory factor treatment is the most obvious; in contrast, that with soluble leukemia inhibitory factor receptor treatment is the most unobvious. Furthermore, the growth of cells with soluble leukemia inhibitory factor receptor and leukemia inhibitory factor co-treatment is worse than that with PBS treatment.

Figure 3B:
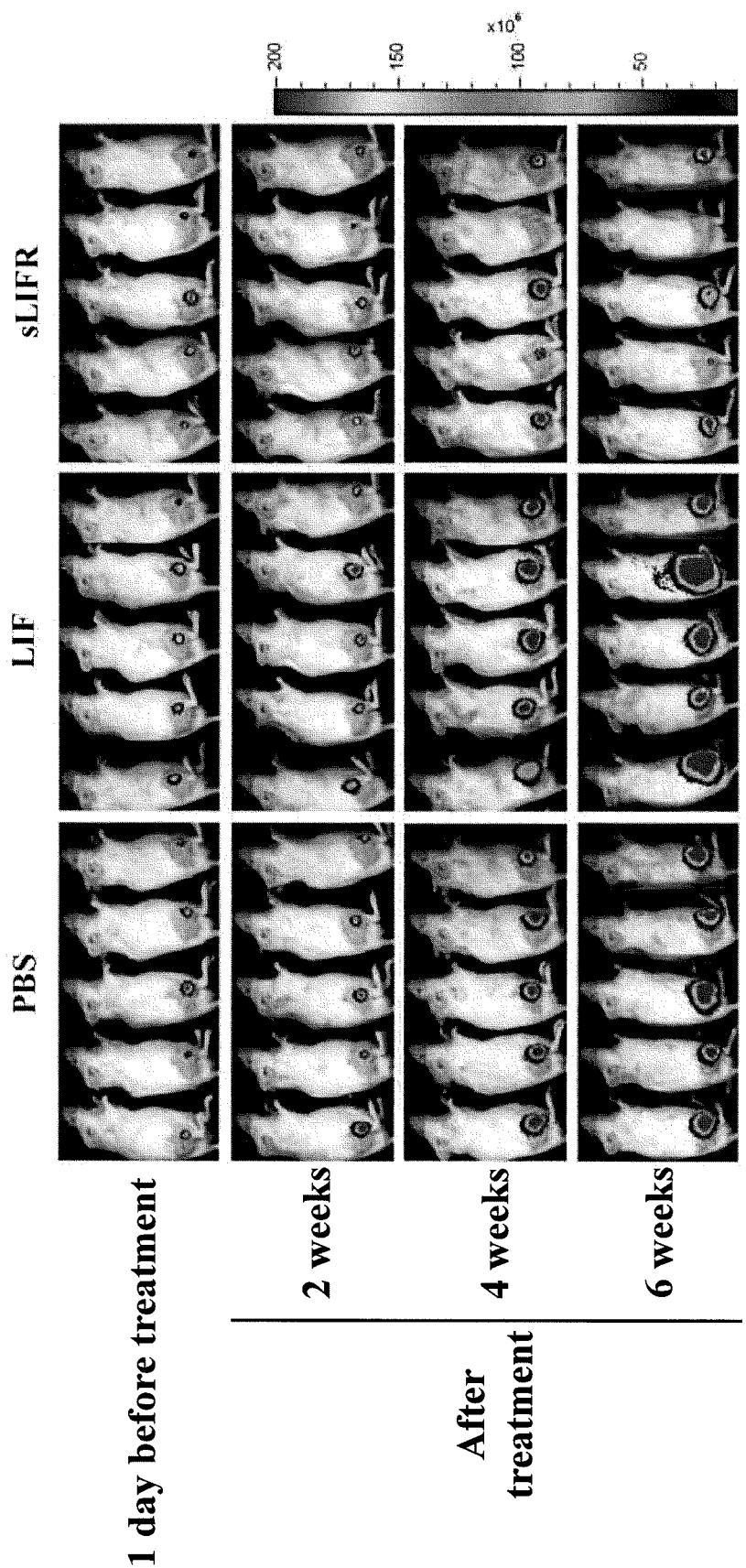
FIG. 3B is a picture demonstrating the tumor growth of a mouse with various substance injection.
Figure 3C:
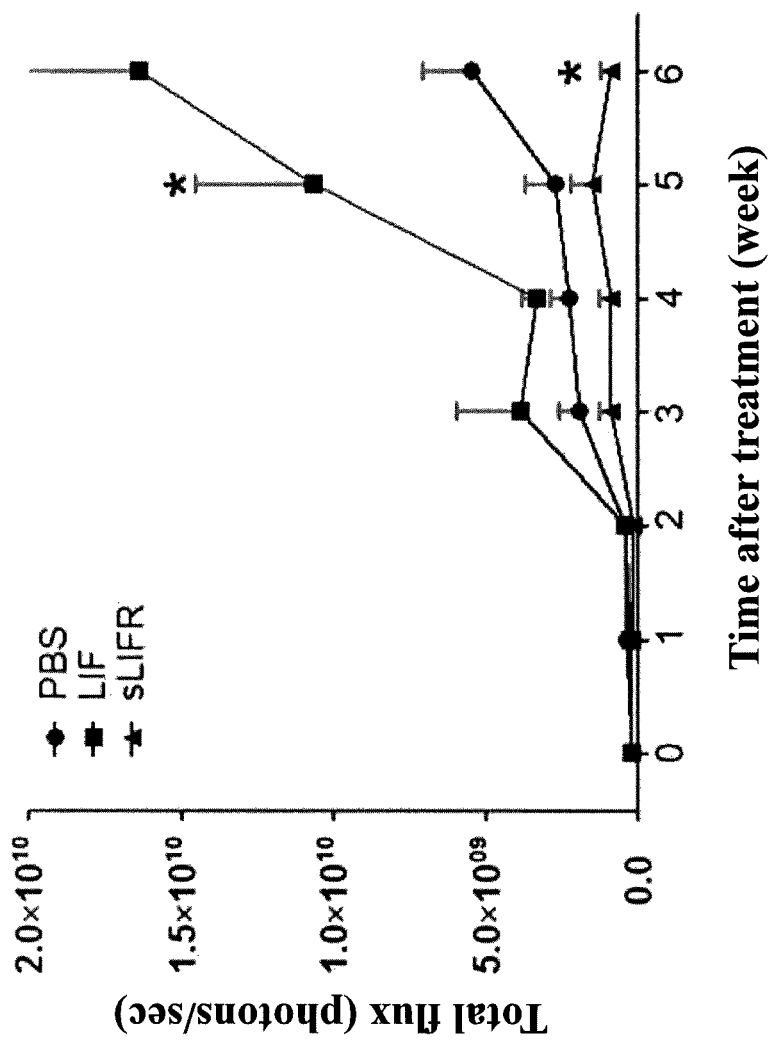
FIG. 3C is a graph displaying the tumor activity of a mouse with various substance injection.

In addition, a TW06 cell transfected with firefly luciferase 2 reporter gene was subcutaneously injected into the thigh of a 7-week-old NOD/SCID (non-obese diabetic/severe-combined immunodeficient) mouse. Until the tumor on the mouse's thigh was grown to a volume of 50 mm$^3$, PBS, leukemia inhibitory factor (150-200 ng, twice per week, 4 weeks), or a soluble leukemia inhibitory factor receptor (1-2 μg, twice per week, 4 weeks) was intratumorally injected into the mouse. Finally, the mouse's tumor was observed, and its activity and volume were detected by an in vivo imaging system at a certain time point after the injection. As shown in FIGS. 3B and 3C, the tumor volume of the mouse with leukemia inhibitory factor injection is the biggest, but that with soluble leukemia inhibitory factor receptor injection is the smallest.

As stated in this example, leukemia inhibitory factor can promote the growth of a nasopharyngeal cancer cell in vivo or in vitro, but a soluble leukemia inhibitory factor receptor cannot.

EXAMPLE 4

Effect of Leukemia Inhibitory Factor on Resistance of a Nasopharyngeal Cancer Cell to Radiation In Vitro Firstly, $6 \times 10^3$ CNE1 cells were seeded. After cultivated at 37° C. overnight, the seeded cells were treated with PBS and leukemia inhibitory factor (10 ng/ml), and then radiation in various doses were emitted to the treated cells. Finally, an xCelligence real time cell analyzer was used to detect the cell growth at a certain time point after this emission.

Figure 4A:
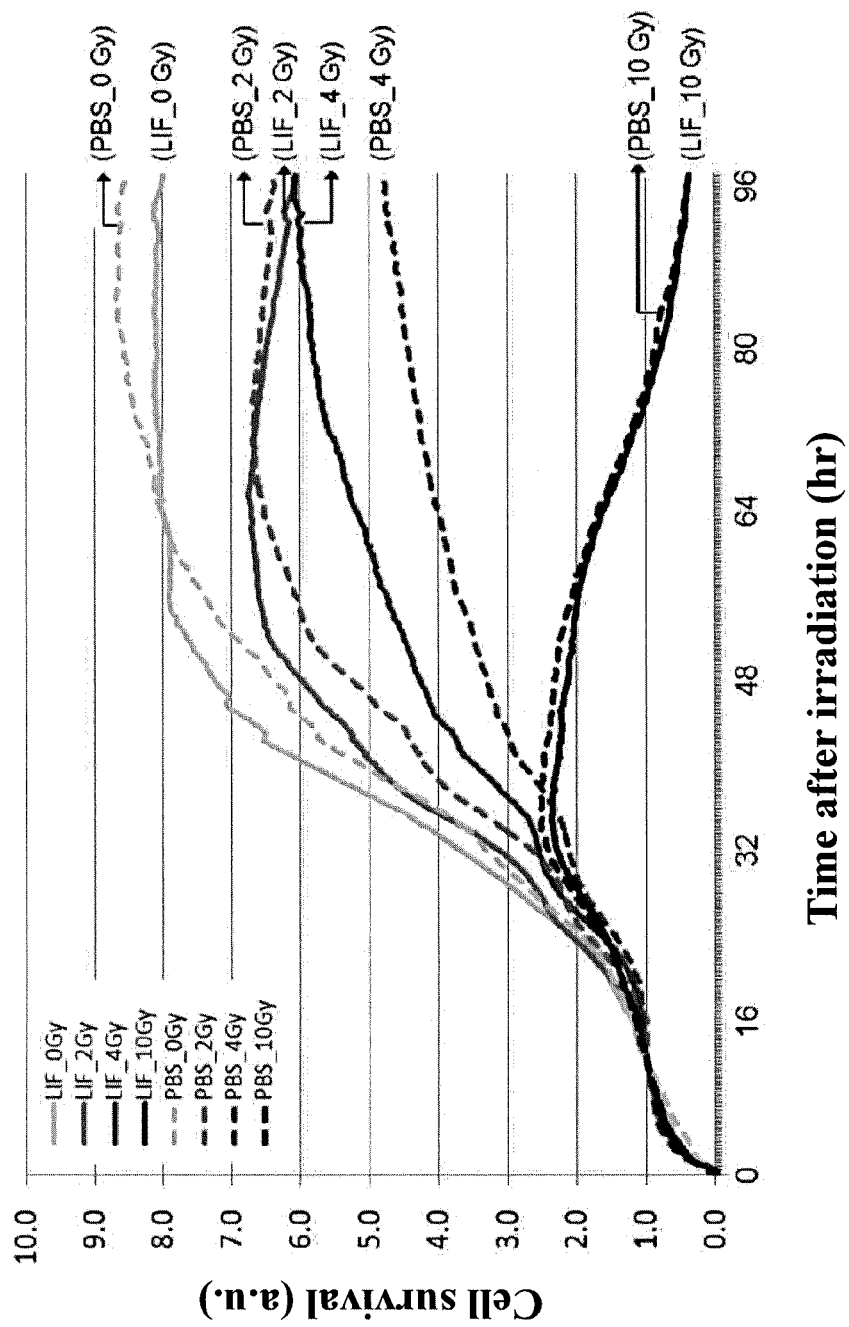
FIG. 4A is a graph showing the survival of a nasopharyngeal cancer cell with various substance treatment and various dose radiation emission.
Figure 4B:
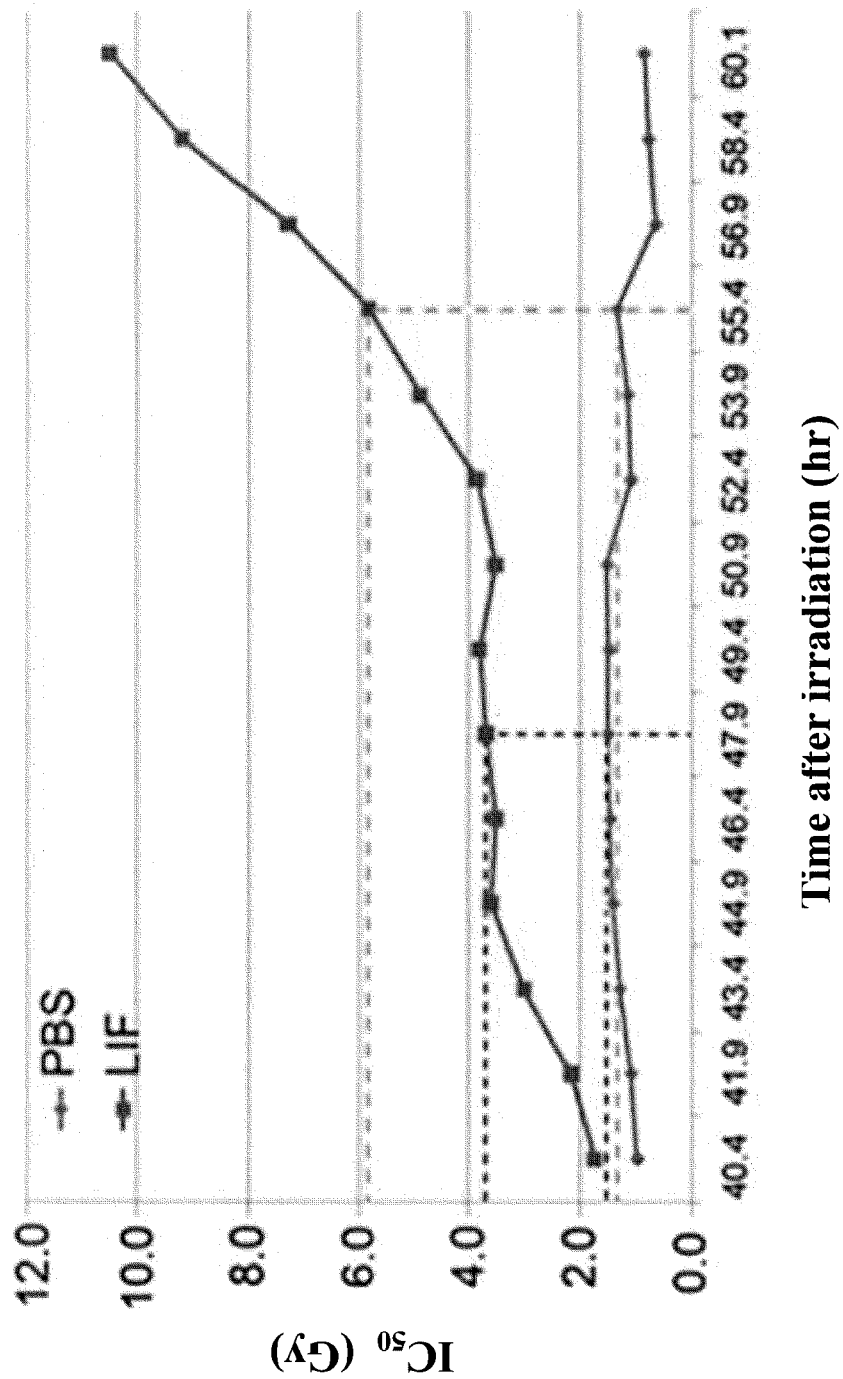
FIG. 4B is a graph presenting an $IC_{50}$ value of radiation for a nasopharyngeal cancer cell with various substance treatment.

As shown in FIG. 4A, the growth of cells with leukemia inhibitory factor treatment and radiation emission is more obvious than that with PBS treatment and radiation emission. As shown in FIG. 4B, at the 48th hour after the radiation emission, the radiation for the cells with PBS treatment has an $IC_{50}$ value of 1.5 Gy, and the radiation for the cells with leukemia inhibitory factor treatment has an $IC_{50}$ value of 3.7 Gy. At the 55th hour after the emission, the radiation for the cells with PBS treatment has an $IC_{50}$ value of 1.3 Gy, and the radiation for the cells with leukemia inhibitory factor treatment has an $IC_{50}$ value of 5.8 Gy.

In another aspect, $6 \times 10^3$ CNE1 cells or TW06 cells were seeded, and then cultivated at 37° C. overnight. The cultivated cells were treated with PBS, a soluble leukemia inhibitory factor receptor (1 µg/ml), leukemia inhibitory factor (10 ng/ml), or leukemia inhibitory factor plus a soluble leukemia inhibitory factor receptor. After which, radiation in 4 Gy were emitted to the treated cells. Finally, an xCelligence real time cell analyzer was used to detect the cell survival at a certain time point after this emission.

Figure 4C:
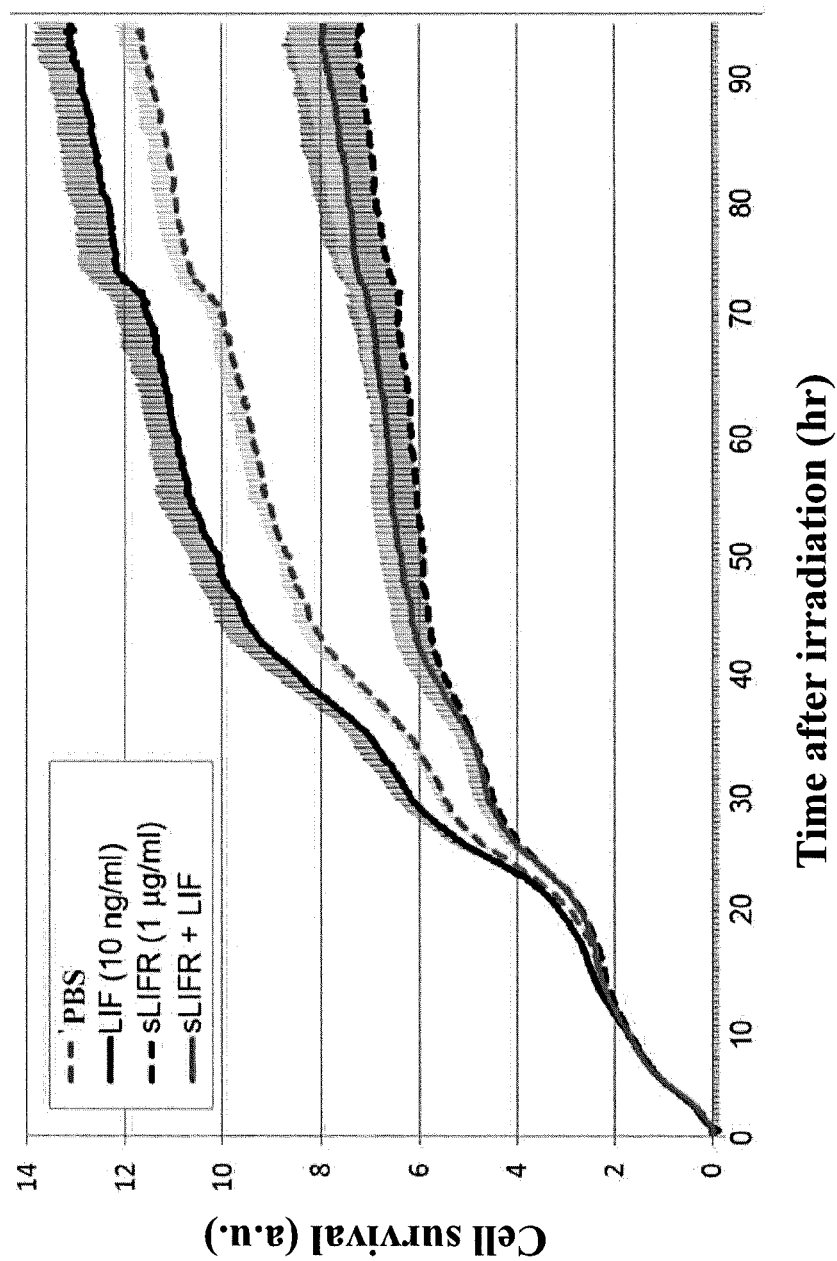
FIG. 4C is a graph illustrating the survival of a nasopharyngeal cancer cell with various substance treatment and emission of radiation in 4 Gy.

As shown in FIG. 4C, the growth of cells with PBS treatment and radiation emission is the most obvious, but that with soluble leukemia inhibitory factor receptor treatment and radiation emission is the most unobvious. Moreover, the growth of cells with soluble leukemia inhibitory factor receptor and leukemia inhibitory factor co-treatment and radiation emission is poorer than that with PBS treatment and radiation emission.

Figure 4D:
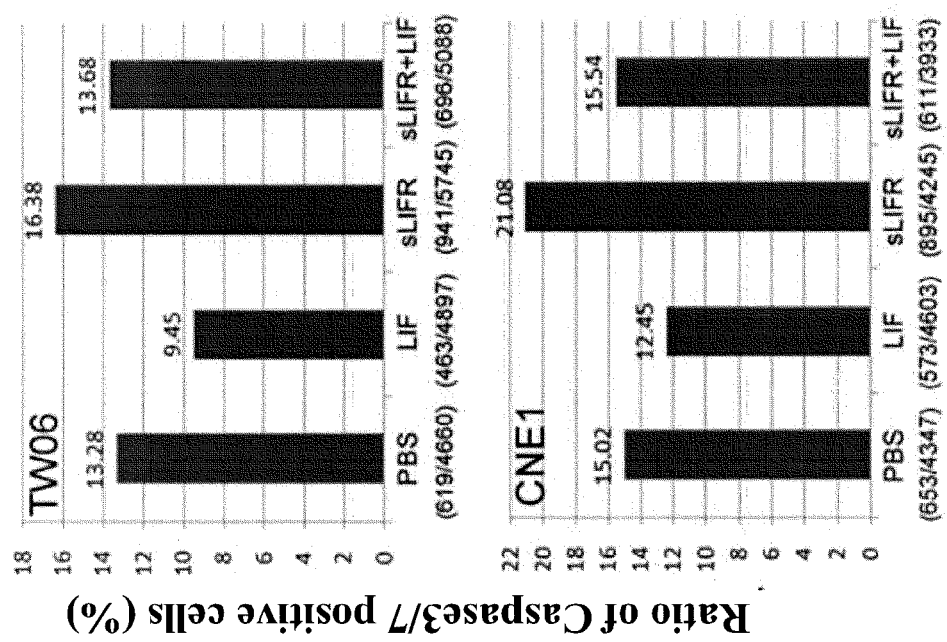
FIG. 4D is a statistical graph showing the ratio of a Caspase3/7 positive cell among a nasopharyngeal cancer cell with various substance treatment and emission of radiation in 4 Gy.
Figure 4E:
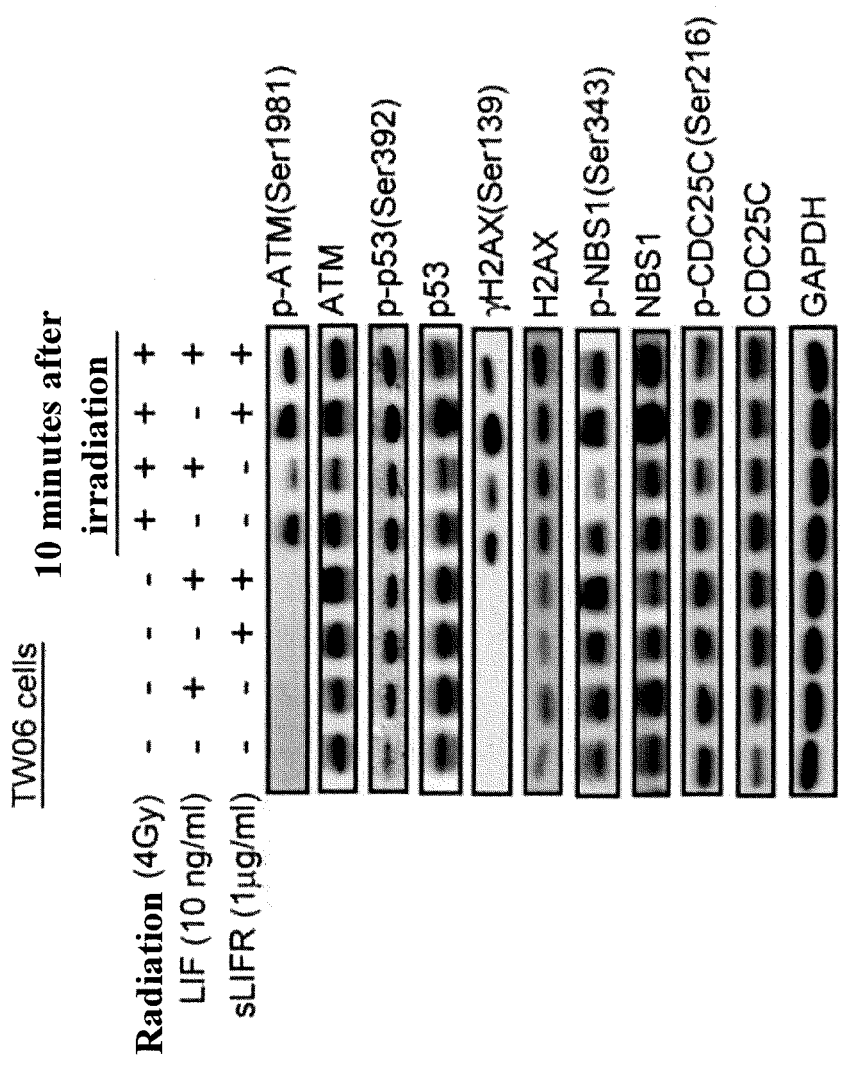
FIG. 4E is a Western blotting result displaying the activation of apoptosis-related and DNA damage-related proteins in TW06 cells with various substance treatment and emission of radiation in 4 Gy.
Figure 4F:
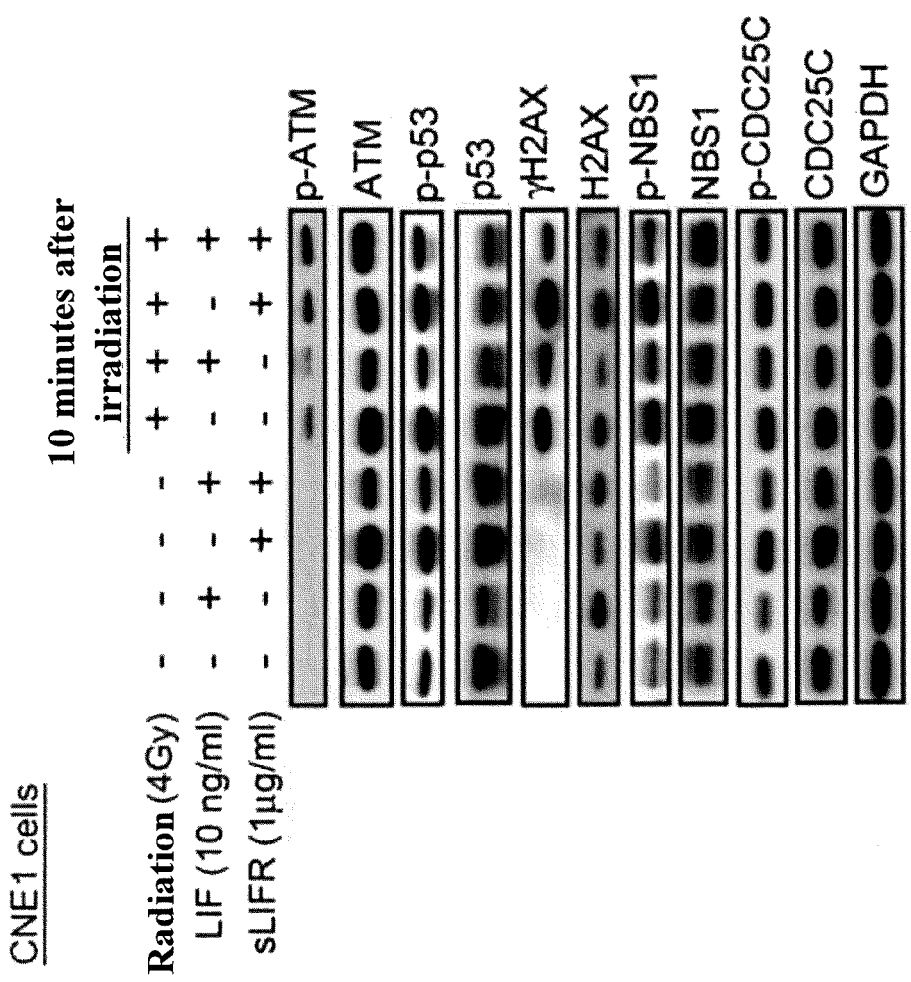
FIG. 4F is a Western blotting result showing the activation of apoptosis-related and DNA damage-related proteins in CNE1 cells with various substance treatment and emission of radiation in 4 Gy.

As shown in FIG. 4D, at the 96th hour after the emission, the cells with leukemia inhibitory factor treatment and radiation emission has low Caspase3/7 expression level as compared with those with soluble leukemia inhibitory factor receptor treatment and radiation emission. As shown in FIGS. 4E and 4F, at the 10th minute following the emission, apoptosis-related and DNA damage-related proteins, i.e. ATM, p53, γH2AX, NBS1 or CDC25C, in the cells are activated/phosphorylated more strongly by the soluble leukemia inhibitory factor receptor plus the emission than by the leukemia inhibitory factor plus the emission.

In summary, leukemia inhibitory factor can enhance resistance of a nasopharyngeal cancer cell to radiation by inhibition of cell death pathway; however, a soluble leukemia inhibitory factor receptor can enhance sensitivity of a nasopharyngeal cancer cell to radiation by promotion of cell death pathway.

EXAMPLE 5

Figure 5A:
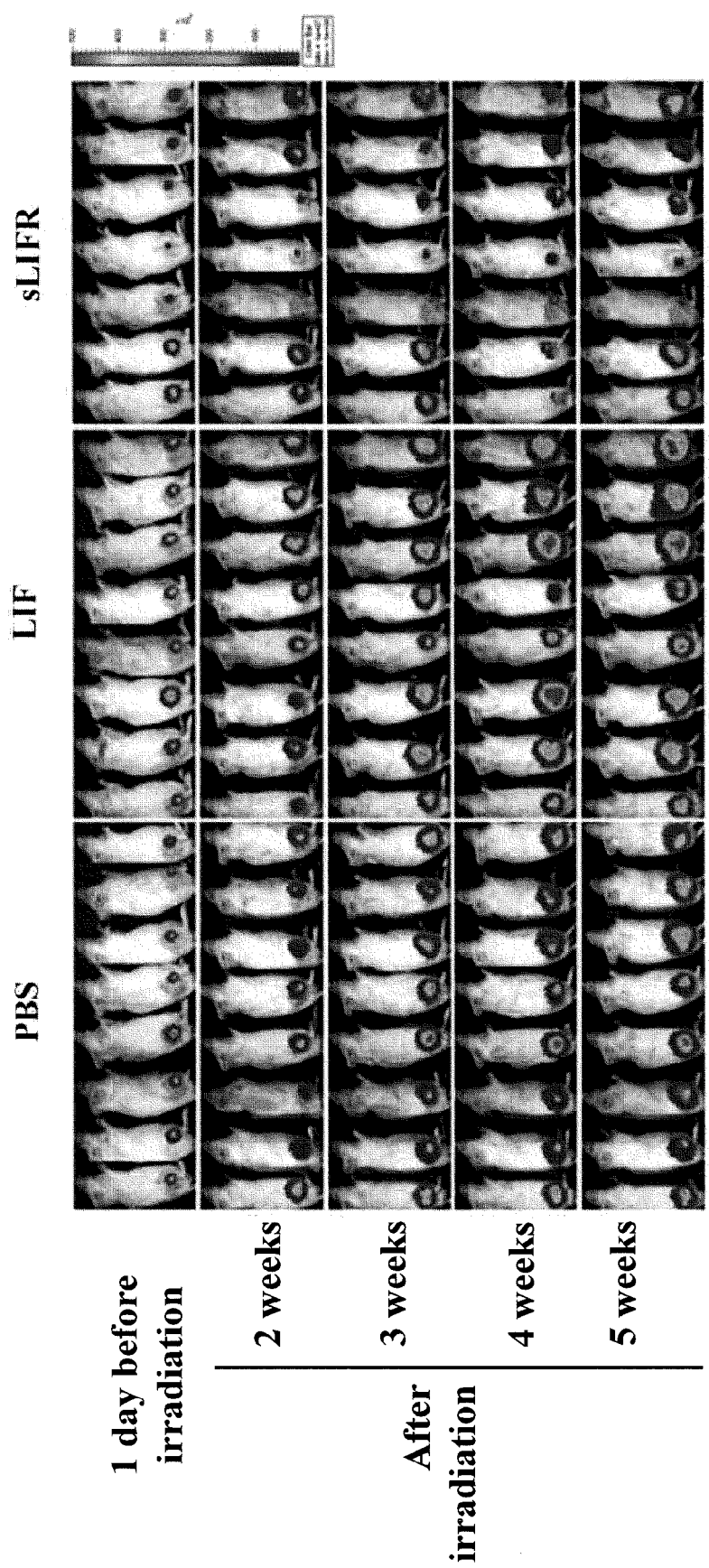
FIG. 5A is a picture presenting the tumor growth of a mouse with various substance treatment and emission of radiation in 7 Gy.
Figure 5B:
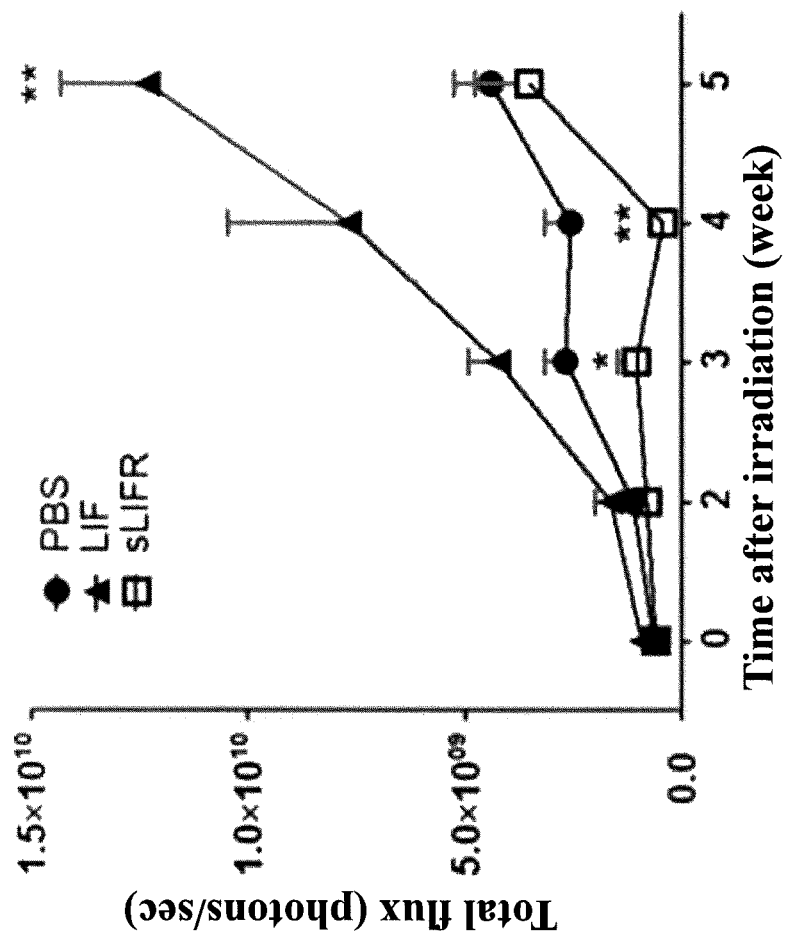
FIG. 5B is a graph illustrating the tumor activity of a mouse with various substance treatment and emission of radiation in 7 Gy.

Effect of Leukemia Inhibitory Factor on Resistance of a Nasopharyngeal Cancer Cell to Radiation In Vivo A TW06 cell transfected with firefly luciferase 2 reporter gene was subcutaneously injected into the thigh of a 7-week-old NOD/SCID mouse. Until the tumor on the thigh was grown to a volume of 60-100 mm$^3$, PBS, leukemia inhibitory factor (150-200 ng, twice per week, 4 weeks), or a soluble leukemia inhibitory factor receptor (1-2 µg, twice per week, 4 weeks) was intratumorally injected into the mouse, and then radiation in a dose of 7 Gy were emitted to the mouse following the first injection. Finally, the mouse's tumor was observed, and its activity and volume were detected by an in vivo imaging system at a certain time point after the emission. As shown in FIGS. 5A and 5B, the tumor volume of the mouse with leukemia inhibitory factor injection and radiation emission is the biggest; however, that with soluble leukemia inhibitory factor receptor injection and radiation emission is the smallest.

Figure 5C:
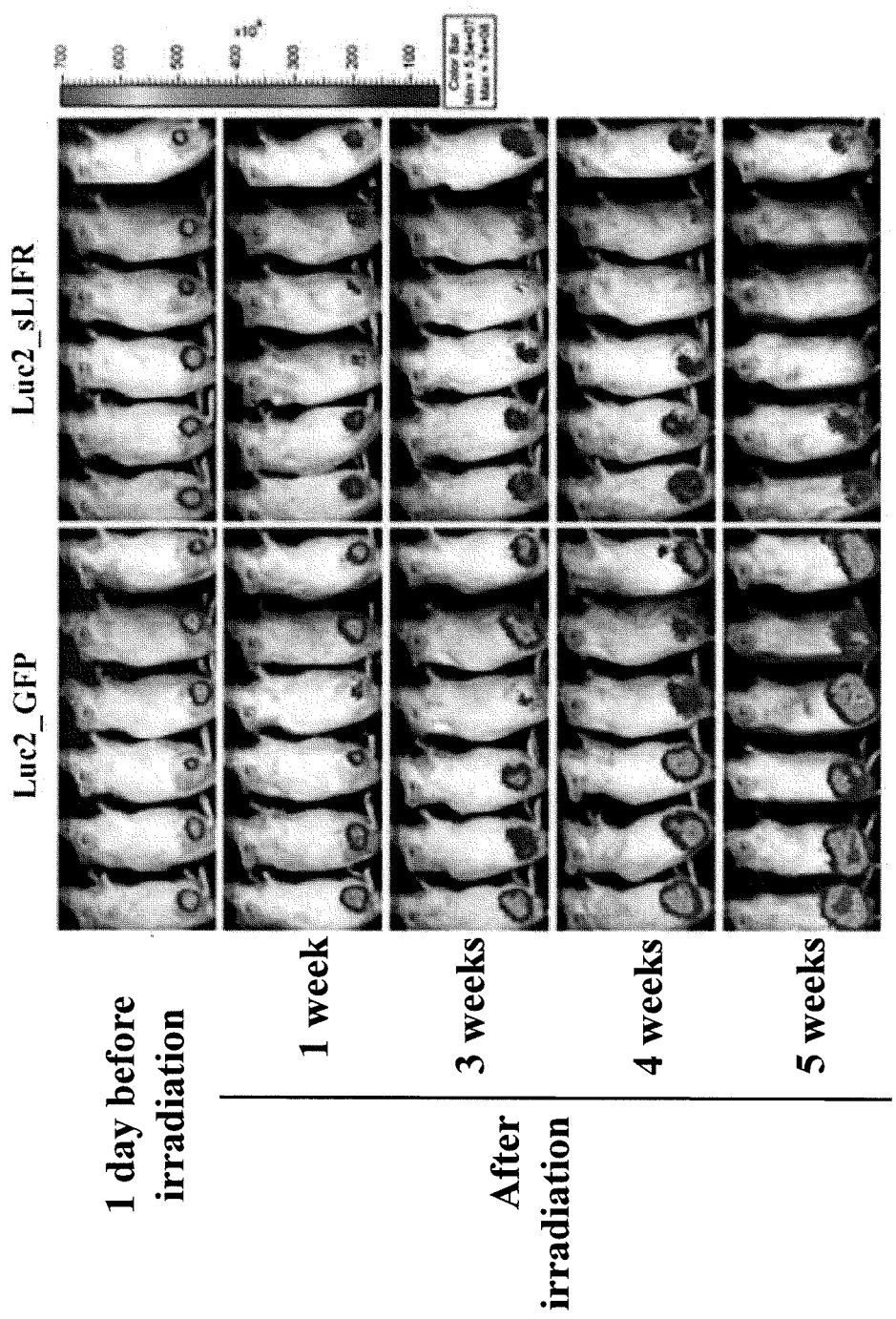
FIG. 5C is a picture demonstrating the tumor growth of a mouse with various transfected cell injection and radiation emission.
Figure 5D:
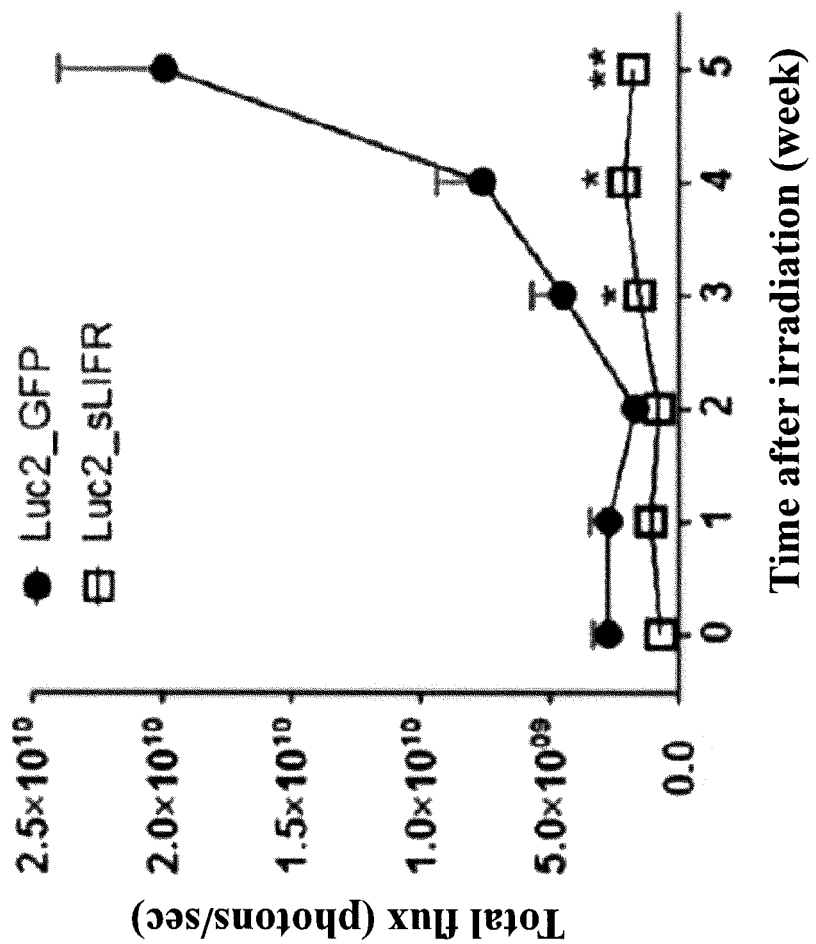
FIG. 5D is a graph displaying the tumor activity of a mouse with various transfected cell injection and radiation emission.

In order to further confirm the foregoing result, a Luc2_sLIFR TW06 cell co-transfected with firefly luciferase 2 reporter gene and soluble leukemia inhibitory factor receptor gene, or a Luc2_GFP TW06 cell co-transfected with firefly luciferase 2 reporter gene and green fluorescent protein (GFP) gene, was subcutaneously injected into the thigh of a 7-week-old NOD/SCID mouse. Until the tumor on the mouse's thigh was grown to a volume of 60-100 mm$^3$, radiation in a dose of 7 Gy were emitted to the mouse. Finally, the mouse's tumor was observed, and its activity and volume were detected by an in vivo imaging system at a certain time point after the emission. As shown in FIGS. 5C and 5D, the tumor volume of the mouse with Luc2_GFP TW06 cell injection is smaller than that with Luc2_sLIFR TW06 cell injection.

In this example, leukemia inhibitory factor can enhance resistance of a nasopharyngeal cancer cell to radiation in vivo, but a soluble leukemia inhibitory factor receptor can enhance sensitivity of a nasopharyngeal cancer cell in vivo.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for enhancing the sensitivity of nasopharyngeal cancer to radiation therapy comprising administering a sensitivity potentiating amount of a leukemia inhibitory factor inhibitor to the subject prior to irradiation.

2. The method as claimed in claim 1, wherein the leukemia inhibitory factor inhibitor is a soluble leukemia inhibitory factor receptor.

3. The method as claimed in claim 1, wherein the leukemia inhibitory factor inhibitor is administrated to the subject intranasally or intratumorally.

4. The method as claimed in claim 1, wherein the leukemia inhibitory factor inhibitor is administrated to the subject intratumorally.

* * * * *

UNITED STATES PATENT AND TRADEMARK OFFICE
CERTIFICATE OF CORRECTION

PATENT NO. : 9,194,872 B2
APPLICATION NO. : 14/250834
DATED : November 24, 2015
INVENTOR(S) : Yu-Sun Chang et al.

It is certified that error appears in the above-identified patent and that said Letters Patent is hereby corrected as shown below:

On the title page, item (54) and in the specification, column 1, line 1, the word "NANOPHARYNGEAL" should read --NASOPHARYNGEAL--

Signed and Sealed this
Fifteenth Day of March, 2016

Michelle K. Lee
*Director of the United States Patent and Trademark Office*